(12) United States Patent
Baldwin et al.

(10) Patent No.: US 10,035,839 B2
(45) Date of Patent: Jul. 31, 2018

(54) BLOOD GLUCOSE LOWERING COMPOUND

(71) Applicants: Eli Lilly and Company, Indianapolis, IN (US); Amunix Operating Inc., Mountain View, CA (US)

(72) Inventors: David Bruce Baldwin, Carmel, IN (US); John Michael Beals, Indianapolis, IN (US); Andrew Ihor Korytko, Oceanside, CA (US); Bryant Rhodius McLaughlin, Millbrae, CA (US); Volker Schellenberger, Palo Alto, CA (US)

(73) Assignees: Eli Lilly and Company, Indianapolis, IN (US); Amunix Operating Inc., Mountain View, CA (US)

( * ) Notice: Subject to any disclaimer, the term of this patent is extended or adjusted under 35 U.S.C. 154(b) by 0 days.

(21) Appl. No.: 15/434,477

(22) Filed: Feb. 16, 2017

(65) Prior Publication Data
US 2017/0240614 A1    Aug. 24, 2017

Related U.S. Application Data

(60) Provisional application No. 62/299,131, filed on Feb. 24, 2016.

(51) Int. Cl.
A61K 38/28    (2006.01)
A61K 47/64    (2017.01)
C07K 14/62    (2006.01)
C07K 19/00    (2006.01)
C07K 14/72    (2006.01)
C07K 14/71    (2006.01)
A61K 38/17    (2006.01)

(52) U.S. Cl.
CPC ............ *C07K 14/72* (2013.01); *A61K 38/179* (2013.01); *A61K 38/1796* (2013.01); *A61K 38/28* (2013.01); *A61K 47/64* (2017.08); *C07K 14/62* (2013.01); *C07K 14/71* (2013.01); *C07K 2319/31* (2013.01)

(58) Field of Classification Search
CPC ........ A61K 38/28; A61K 47/64; C07K 14/62; C07K 2319/31
See application file for complete search history.

(56) References Cited

U.S. PATENT DOCUMENTS

| 5,656,722 A | 8/1997 | Dorschug |
| 9,050,371 B2 | 6/2015 | Beals et al. |
| 2015/0037359 A1* | 2/2015 | Schellenberger .... C07K 5/0205 424/178.1 |

FOREIGN PATENT DOCUMENTS

| WO | 2013130683 | 9/2013 |
| WO | 2013130684 A1 | 9/2013 |
| WO | 2013169547 A1 | 11/2013 |

OTHER PUBLICATIONS

Henry, *Basal Insulin Peglispro Demonstrates Preferential Hepatic Versus Peripheral Action Relative to Insulin Glargine in Healthy Subjects*, Diabetes Care, 2014, 2609-2615, 37:.

Strohl, W. R. (2015). Fusion proteins for half-life extension of biologics as a strategy to make biobetters. *BioDrugs*, 29(4), 215-239.

Scheilenberger, V., Wang, C. W., Geething, N. C., Spink, B. J., Campbell, A., To, W., . . . & Cleland, J. L. (2009). A recombinant polypeptide extends the in vivo half-life of peptides and proteins in a tunable manner. *Nature biotechnology*, 27(12), 1186-1190.

* cited by examiner

*Primary Examiner* — Jeffrey E Russel
(74) *Attorney, Agent, or Firm* — Jennifer K Gregory

(57) ABSTRACT

The present invention relates to the field of medicine and the treatment of diabetes or hyperglycemia within that field. More particularly, the invention relates to a compound that lowers blood glucose, pharmaceutical compositions containing such a compound, and therapeutic uses of such a compound. The compound claimed herein comprises an A chain and a B chain, wherein the amino acid sequence of the A chain is SEQ ID NO: 1 and the amino acid sequence of the B chain is SEQ ID NO: 2.

6 Claims, No Drawings

SEQUENCE LISTING

<160> NUMBER OF SEQ ID NOS: 4

<210> SEQ ID NO 1
<211> LENGTH: 315
<212> TYPE: PRT
<213> ORGANISM: Artificial Sequence
<220> FEATURE:
<223> OTHER INFORMATION: Synthetic Construct

<400> SEQUENCE: 1

Gly Ile Val Glu Gln Cys Cys Thr Ser Ile Cys Ser Leu Tyr Gln Leu
1               5                   10                  15

Glu Asn Tyr Cys Gly Ser Gly Pro Ala Gly Thr Ser Glu Ser Ala
            20                  25                  30

Thr Pro Glu Ser Gly Pro Gly Ser Glu Pro Ala Thr Ser Gly Ser Glu
            35                  40                  45

Thr Pro Gly Thr Ser Glu Ser Ala Thr Pro Glu Ser Gly Pro Gly Ser
        50                  55                  60

Glu Pro Ala Thr Ser Gly Ser Glu Thr Pro Gly Thr Ser Glu Ser Ala
65                  70                  75                  80

Thr Pro Glu Ser Gly Pro Gly Thr Ser Thr Glu Pro Ser Glu Gly Ser
                85                  90                  95

Ala Pro Gly Ser Pro Ala Gly Ser Pro Thr Ser Thr Glu Glu Gly Thr
                100                 105                 110

Ser Glu Ser Ala Thr Pro Glu Ser Gly Pro Gly Ser Glu Pro Ala Thr
            115                 120                 125

Ser Gly Ser Glu Thr Pro Gly Thr Ser Glu Ser Ala Thr Pro Glu Ser
        130                 135                 140

Gly Pro Gly Ser Pro Ala Gly Ser Pro Thr Ser Thr Glu Glu Gly Ser
145                 150                 155                 160

Pro Ala Gly Ser Pro Thr Ser Thr Glu Glu Gly Thr Ser Thr Glu Pro
                165                 170                 175

Ser Glu Gly Ser Ala Pro Gly Thr Ser Glu Ser Ala Thr Pro Glu Ser
            180                 185                 190

Gly Pro Gly Thr Ser Glu Ser Ala Thr Pro Glu Ser Gly Pro Gly Thr
            195                 200                 205

Ser Glu Ser Ala Thr Pro Glu Ser Gly Pro Gly Ser Glu Pro Ala Thr
            210                 215                 220

Ser Gly Ser Glu Thr Pro Gly Ser Glu Pro Ala Thr Ser Gly Ser Glu
225                 230                 235                 240

Thr Pro Gly Ser Pro Ala Gly Ser Pro Thr Ser Thr Glu Glu Gly Thr
                245                 250                 255

Ser Thr Glu Pro Ser Glu Gly Ser Ala Pro Gly Thr Ser Thr Glu Pro
            260                 265                 270

Ser Glu Gly Ser Ala Pro Gly Ser Glu Pro Ala Thr Ser Gly Ser Glu
            275                 280                 285

Thr Pro Gly Thr Ser Glu Ser Ala Thr Pro Glu Ser Gly Pro Gly Thr
            290                 295                 300

Ser Thr Glu Pro Ser Glu Gly Ser Ala Pro Gly
305                 310                 315

<210> SEQ ID NO 2
<211> LENGTH: 30
<212> TYPE: PRT
<213> ORGANISM: Artificial Sequence
<220> FEATURE:
<223> OTHER INFORMATION: Synthetic Construct

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

```
<210> SEQ ID NO 3
<211> LENGTH: 432
<212> TYPE: PRT
<213> ORGANISM: Artificial Sequence
<220> FEATURE:
<223> OTHER INFORMATION: Synthetic Construct

<400> SEQUENCE: 3

Met Lys Lys Asn Ile Ala Phe Leu Leu Ala Ser Met Phe Val Phe Ser
1               5                   10                  15

Ile Ala Thr Asn Ala Tyr Ala Gly Ser Pro Gly Thr Ser Thr Glu Pro
            20                  25                  30

Ser Glu Gly Ser Ala Pro Gly Thr Ser Glu Ser Ala Thr Pro Glu Ser
        35                  40                  45

Gly Pro Gly Thr Ser Glu Ser Ala Thr Pro Glu Ser Gly Pro Gly Gly
    50                  55                  60

Ala Pro Gly Ser Gly Ser Gly Gly Ser Gly Gly Ile Glu Gly
65                  70                  75                  80

Arg Phe Val Asn Gln His Leu Cys Gly Ser His Leu Val Glu Ala Leu
                85                  90                  95

Tyr Leu Val Cys Gly Glu Arg Gly Phe Phe Tyr Thr Lys Pro Thr Arg
            100                 105                 110

Gly Gly Gly Gly Arg Gly Ile Val Glu Gln Cys Cys Thr Ser Ile Cys
        115                 120                 125

Ser Leu Tyr Gln Leu Glu Asn Tyr Cys Gly Ser Gly Pro Ala Gly Gly
    130                 135                 140

Thr Ser Glu Ser Ala Thr Pro Glu Ser Gly Pro Gly Ser Glu Pro Ala
145                 150                 155                 160

Thr Ser Gly Ser Glu Thr Pro Gly Thr Ser Glu Ser Ala Thr Pro Glu
                165                 170                 175

Ser Gly Pro Gly Ser Glu Pro Ala Thr Ser Gly Ser Glu Thr Pro Gly
            180                 185                 190

Thr Ser Glu Ser Ala Thr Pro Glu Ser Gly Pro Gly Thr Ser Thr Glu
        195                 200                 205

Pro Ser Glu Gly Ser Ala Pro Gly Ser Pro Ala Gly Ser Pro Thr Ser
    210                 215                 220

Thr Glu Glu Gly Thr Ser Glu Ser Ala Thr Pro Glu Ser Gly Pro Gly
225                 230                 235                 240

Ser Glu Pro Ala Thr Ser Gly Ser Glu Thr Pro Gly Thr Ser Glu Ser
                245                 250                 255

Ala Thr Pro Glu Ser Gly Pro Gly Ser Pro Ala Gly Ser Pro Thr Ser
            260                 265                 270

Thr Glu Glu Gly Ser Pro Ala Gly Ser Pro Thr Ser Thr Glu Glu Gly
        275                 280                 285

Thr Ser Thr Glu Pro Ser Glu Gly Ser Ala Pro Gly Thr Ser Glu Ser
    290                 295                 300

Ala Thr Pro Glu Ser Gly Pro Gly Thr Ser Glu Ser Ala Thr Pro Glu
305                 310                 315                 320

Ser Gly Pro Gly Thr Ser Glu Ser Ala Thr Pro Glu Ser Gly Pro Gly
                325                 330                 335

Ser Glu Pro Ala Thr Ser Gly Ser Glu Thr Pro Gly Ser Glu Pro Ala
            340                 345                 350

Thr Ser Gly Ser Glu Thr Pro Gly Ser Pro Ala Gly Ser Pro Thr Ser
        355                 360                 365
```

```
Thr Glu Glu Gly Thr Ser Thr Glu Pro Ser Glu Gly Ser Ala Pro Gly
    370                 375                 380
Thr Ser Thr Glu Pro Ser Glu Gly Ser Ala Pro Gly Ser Glu Pro Ala
385                 390                 395                 400
Thr Ser Gly Ser Glu Thr Pro Gly Thr Ser Glu Ser Ala Thr Pro Glu
                405                 410                 415
Ser Gly Pro Gly Thr Ser Thr Glu Pro Ser Glu Gly Ser Ala Pro Gly
                420                 425                 430

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Thr Glu Thr Ser Gln Val Ala Pro Ala
1               5
```

BLOOD GLUCOSE LOWERING COMPOUND

The present invention relates to the field of medicine. More particularly, the invention is in the field of treatment of diabetes and hyperglycemia. The invention relates to a compound that lowers blood glucose, pharmaceutical compositions containing such a compound and therapeutic uses of such a compound.

Insulin replacement therapy for diabetic patients ideally would parallel as closely as possible the pattern of endogenous insulin secretion in healthy individuals. The physiological demand for insulin may be separated into two phases: (a) a nutrient absorptive phase requiring a pulse of insulin to dispose of the meal-related blood glucose surge, also known as "prandial" insulin, and (b) a post-absorptive phase requiring a sustained delivery of insulin to regulate hepatic glucose output for maintaining optimal fasting blood glucose, also known as a "basal" insulin.

Effective insulin therapy for people with diabetes generally may involve the combined use of two types of exogenous insulin formulations: a rapid-acting, mealtime prandial insulin, and a longer-acting basal insulin administered once or twice daily to control blood glucose levels between meals. One goal of insulin therapy is to mimic the normal pattern of endogenous insulin secretion and activity as closely as possible without causing hypoglycemia. Characteristics of endogenous insulin that may be desirable to emulate include a binding affinity for the human insulin receptors, preferential binding to the human insulin receptors over the human IGF-1 receptor, phosphorylation of the human insulin receptors, and glucose lowering in the blood. Another desirable property of exogenous insulin may be to mimic the activity of endogenous insulin in the liver and peripheral tissues.

A desirable exogenous basal insulin should also provide an extended and "flat" time action—that is, it would control blood glucose levels for at least 12 hours, and preferably for 24 hours or longer, without significant risk of hypoglycemia. Some basal insulins have a duration of action of 24 hours or more, but insulins with an even longer duration of action may assist more patients in achieving better glycemic control. A compound with an extended duration of action, such as a period greater than 24 hours, may lower the risk of nocturnal hypoglycemia and allow greater variability in daily dosing times without increasing a patient's risk of hypoglycemia. WO13130683 generally describes extending the half-life of peptides through the use of a protein conjugate.

The need exists for a new and improved basal insulin compound with an extended and flat duration of action profile to treat diabetes and hyperglycemia in patients in need thereof.

The present compound comprises an insulin compound which provides an extended and flat time action and which has been shown to control blood glucose levels for up to 72 hours. The insulin compound of the present invention is projected to have a flat pharmacokinetic profile with daily dosing, with low peak-to-trough ratios during its extended duration of action. In an embodiment, the present invention provides a compound that is useful in treating diabetes, reducing hemoglobin A1c, and reducing blood glucose levels in patients in need thereof. The compound of the present invention demonstrates glucose lowering of up to 89% and duration of action of up to 72 hours.

The present invention provides an insulin compound comprising an A chain and a B chain, wherein the amino acid sequence of the A chain is SEQ ID NO: 1 and the B chain is SEQ ID NO: 2; and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A chain. The compound of the present invention may be referred to herein as Compound 330.

The present invention also provides a pharmaceutical composition comprising a compound comprising an A chain and a B chain, wherein the amino acid sequence of the A chain is SEQ ID NO: 1 and the B chain is SEQ ID NO: 2; and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A chain and one or more pharmaceutically acceptable excipients.

The present invention further provides a method of treating diabetes or hyperglycemia in a patient comprising administering to a patient in need thereof an effective amount of a compound comprising an A chain and a B chain, wherein the amino acid sequence of the A chain is SEQ ID NO: 1 and the B chain is SEQ ID NO: 2; and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A chain. In a further embodiment, the present invention provides a method of treating diabetes or hyperglycemia in a patient comprising administering an effective amount to a patient in need thereof of a pharmaceutical composition comprising a compound comprising an A chain and a B chain, wherein the amino acid sequence of the A chain is SEQ ID NO: 1 and the B chain is SEQ ID NO: 2; and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A and one or more pharmaceutically acceptable excipients.

The present invention provides a compound comprising an A chain and a B chain, wherein the amino acid sequence of the A chain is SEQ ID NO: 1 and the B chain is SEQ ID NO: 2; and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A chain for use in therapy. The present invention further provides a compound comprising an A chain and a B chain, wherein the amino acid sequence of the A chain is SEQ ID NO: 1 and the B chain is SEQ ID NO: 2; and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A chain for use in the treatment of diabetes. In a further embodiment, the present invention provides a compound comprising an A chain and a B chain, wherein the amino acid sequence of the A chain is SEQ ID NO: 1 and the B chain is SEQ ID NO: 2; and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A chain for use in the treatment of hyperglycemia.

The present invention also provides the use of a compound comprising an A chain and a B chain, wherein the amino acid sequence of the A chain is SEQ ID NO: 1 and the B chain is SEQ ID NO: 2; and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A chain in the manufacture of a medicament for the treatment of diabetes. The present invention provides the use of a compound comprising an A chain and a B chain, wherein the amino acid sequence of the A chain is SEQ ID NO: 1 and the B chain is SEQ ID NO: 2; and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A chain in the manufacture of a medicament for the treatment of hyperglycemia.

The term "treatment" or "treating" as used herein refers to the management and care of a patient having diabetes or hyperglycemia, or other condition for which insulin administration is indicated for the purpose of combating or alleviating symptoms and complications of those conditions. Treating includes administering a compound or compositions containing a compound of the present invention to a patient in need thereof to prevent the onset of symptoms or complications, alleviating the symptoms or complications, or eliminating the disease, condition, or disorder. The patient to be treated is an animal, and preferably a human being.

As used herein, the term "effective amount" refers to the amount or dose of a compound of the present invention or a pharmaceutical composition containing a compound of the present invention, which upon single or multiple dose administration to the patient or subject, will elicit the biological or medical response of or desired therapeutic effect on a tissue, system, animal, mammal or human that is being sought by the researcher, veterinarian, medical doctor or other clinician. A dose can include a higher initial loading dose, followed by a lower dose.

The terms "patient," "subject," and "individual," used interchangeable herein, refer to an animal, preferably the terms refer to humans. In certain embodiments, the patient, preferably a human, is further characterized with a disease or disorder or condition that would benefit from lowering glucose levels in the blood.

Pharmaceutical compositions comprising the compound of the present invention may be administered parenterally to patients in need of such treatment. Parenteral administration may be performed by subcutaneous, intramuscular or intravenous injection by means of a syringe, optionally a pen-like syringe, or mechanical driven injector. Alternatively, parenteral administration can be performed by means of an infusion pump. Embodiments of the present invention provide pharmaceutical compositions suitable for administration to a patient comprising administering to a patient in need thereof a therapeutically effective amount of a compound of the present invention and one or more pharmaceutically acceptable excipients. Such pharmaceutical compositions may be prepared by any of a variety of techniques using conventional excipients for pharmaceutical products which are well known in the art. (Remington's Pharmaceutical Sciences, 21st Edition, University of the Sciences in Philadelphia, Philadelphia, Pa., USA (2006)).

The compound of the present invention may be prepared by a variety of techniques known to one of skill in the art. The compound may be prepared via a precursor protein molecule using recombinant DNA techniques. The DNA, including cDNA and synthetic DNA, may be double-stranded or single-stranded. The coding sequences that encode the precursor protein molecule described herein may vary as a result of the redundancy or degeneracy of the genetic code. The DNA may be introduced into a host cell in order to produce the precursor protein of the present invention. The host cells may be bacterial cells such as K12 or B strains of *Escherichia coli*, fungal cells such as yeast cells, or mammalian cells such as chinese hamster ovary ("CHO") cells.

The compound of the present invention may be prepared via a precursor protein having the amino acid sequence of SEQ ID NO: 3. An appropriate host cell is either transiently or stably transfected or transformed with an expression system for producing the precursor protein of the present invention. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit selection of those cells transformed with the desired DNA sequences.

Plasmids based on a modified pBR322 plasmid may be used for expression and expression from the plasmids may be induced by a PhoA promoter. The precursor protein may include a secretion signal to enable it to be secreted into the cell periplasm. Accumulation of the precursor protein may occur in any of the cytoplasm, the periplasm, and the extracellular growth media. The precursor protein folds and disulfide bonds are formed during the folding process. After a two to four day fermentation, the precursor protein product may be harvested from the medium, from the cell periplasm and/or from a total cell lysate.

The compound of the present invention may be prepared by a variety of procedures known in the art, as well as those methods described below. The specific synthetic steps for each of the routes described may be combined in different ways to prepare the compound of the invention.

EXAMPLE 1

Expression and Purification of Compound 330

A precursor protein for Compound 330 is expressed in B strain *E. coli* bacteria, strain BL21 from New England Biolabs, product #C2530H. The precursor protein is produced from a modified pBR322 plasmid, whose gene is regulated by a phoA promoter. Typical fermentations are run from 36-72 hours during which the protein is secreted into the media.

Medium is conditioned by lowering the pH with glacial acetic acid. At a pH of 4, many contaminating proteins, lipids, cellular debris, and other matter precipitate and are removed by centrifugation. This conditioned media is put through a depth filter prior to an ultrafiltration/diafiltration ("UFDF") step designed to remove salt and exchange the protein into 5 mM acetate, 10 mM NaCl, pH 4. The precursor protein is captured at low pH on Big Bead Q resin, an anion exchanger with large pore sizes to allow the passage of fines and other debris from the fermentation. The charged resin is washed and the precursor protein is eluted by salt gradient.

The pool from the anion exchange is treated with trypsin and carboxipeptidase B to remove regions of the precursor protein, generating a two-chain insulin. The cleavage process is performed at pH 7.5, and 15° C., for 24 hours. The reaction is quenched by lowering the pH to 4 via acid addition. The resulting solution is concentrated and diafiltered by TFF into 5 mM Acetate, pH 4.

The compound is captured by a cation exchanger (Fast Flow S Sepharose) selected for its ability to bind the positively charged portion of the compound. The charged resin is washed and the compound is eluted by salt gradient. The pool from the cation exchange step is further purified by reversed phase chromatography. The compound is bound to a YMC basic C8 resin with 10 µm bead size in the presence of 0.16% phosphoric acid, and is eluted by an acetonitrile gradient. The final pool is prepared for storage by an overnight dialysis step, followed by concentration, and buffer exchange using spin concentrators to place it in a final buffer of 20 mM Tris, 135 mM NaCl, pH 7.5.

In Vitro Receptor Affinity

Binding affinities of proteins are determined in receptor binding assays performed on membranes prepared from stably-transfected 293EBNA cells (293HEK human embryonic kidney cells expressing EBNA-1) over-expressing human insulin receptor isoform A (hIR-A), stably transfected 293HEK cells over-expressing human insulin receptor isoform B (hIR-B) containing a C9 epitope tag (SEQ ID NO: 4) at the C-terminus, or stably transfected 293HEK cells over-expressing the human IGF-1 receptor (hIGF-1R).

Receptor binding affinities ($K_i$) are determined from a competitive radioligand binding assay using either human recombinant (3-[$^{125}$I]-iodotyrosyl-A14)-insulin (2200 Ci/mmol, for hIR-A and hIR-B assays) or human recombinant [$^{125}$I]-insulin-like growth factor-1 (1800 to 2600 Ci/mmol, for the hIGF-1R assay), (Perkin Elmer Life and Analytical Sciences). The assays are performed with a scintillation proximity assay (SPA) method using polyvinyltoluene (PVT) wheat germ agglutinin-coupled SPA beads (Perkin Elmer Life and Analytical Sciences). SPA Assay Buffer (50 mM Tris-HCl, pH 7.5, 150 mM NaCl, 0.1% w/v fatty-acid free BSA) is used for all reagent preparations.

Serial dilutions of test samples are prepared in Assay Buffer using a Freedom/Evo robot (Tecan) and 50 µL of dilution added to 96-well white, clear-bottom microplates (Corning/Costar) with a TeMO robot (Tecan). Radioligand (50 µL), membranes (50 µL), and SPA beads (50 µL) are added using a Multi-drop (Thermo Scientific) instrument. Following 10-hour incubation at room temperature, radioactivity is determined using a Microbeta Trilux scintillation counter (Perkin Elmer Life and Analytical Sciences).

Values for test samples are calculated as percent relative to the activity of unlabeled human insulin or IGF-1 after correcting for non-specific binding. $IC_{50}$ values are determined from 4-parameter logistic non-linear regression analysis (XLFit version 4.0, IDBS). If necessary, curve top or bottom parameters are set to 100 or 0, respectively. The affinity constant ($K_i$) is calculated from the $IC_{50}$ value based upon the equation, $K_i=IC_{50}/(1+D/K_d)$, where D equals the concentration of radio-ligand used in the experiment and $K_d$ equals the equilibrium binding affinity constant of the radio-ligand determined from saturation binding analysis (hIR-A=0.251 nM; hIR-B=0.205 nM; hIGF-1R=0.233 nM). Reported values for Ki are shown as geometric mean± the standard error of the mean (SEM), with the number of replicate determinations indicated by "n" (Table 1). A qualifier (>) indicates that the data does not reach 50% inhibition, compared to maximum binding, whereby the $K_i$ is calculated using the highest concentration of the compound tested in the assay and no standard error is calculated.

Compound 330 has binding affinity at both hIR-A and hIR-B and selectivity over hIGF-1R (Table 1).

TABLE 1

Human Insulin Receptor Isoform A or B (hIR-A or hIR-B) and Human Insulin-Like Growth Factor-1 Receptor (hIGF-1R) Binding Affinity

| | Receptor Binding Affinity, $K_i$, nM (SEM, n) | | |
|---|---|---|---|
| Sample | hIR-A | hIR-B | hIGF-1R |
| Compound 330 | 4.53 (0.63, n = 10) | 6.07 (0.60, n = 10) | >3530 (n = 5) |
| Human insulin | 0.189 (0.006, n = 45) | 0.233 (0.008, n = 45) | 80.1 (5.8, n = 35) |
| IGF-1 | 4.10 (0.26, n = 45) | 50.8 (2.7, n = 45) | 0.111 (0.008, n = 33) |

Receptor Functional Activation

Functional activity is determined by ELISA quantitation of hIR-A, hIR-B, or hIGF-1R auto-phosphorylation. Stably-transfected human 293HEK cells that over express hIR-A, hIR-B, or hIGF-1R, each containing a C-terminal C9 epitope tag (TETSQVAPA (SEQ ID NO: 4)), are treated at 37° C. for 1 hour with 3-fold serially diluted test compounds in serum-free medium (DMEM, high glucose with glutamine, 10 mM HEPES, pH 7.4, 1 mM sodium pyruvate, 0.8 mg/mL geneticin, 1% penicillin/streptomycin) supplemented with 0.1% fraction V-fatty acid-free BSA (Sigma-Aldrich (St. Louis, Mo., USA)). Cells are rinsed with ice cold PBS and lysed with ice cold NP40 buffer [1% NP-40 (IGEPAL CA-630), 150 mM NaCl, 50 mM TRIS, pH 7.4, 2 mM vanadate, and Complete™ protease inhibitors].

Tyrosine phosphorylation is determined using a sandwich ELISA by capture with anti-C9 monoclonal antibody (RHO 1D4 Antibody, University of British Columbia) and detection with anti-phosphotyrosine monoclonal 4G10®-horseradish peroxidase (4G10®-HRP) conjugate (EMD Millipore, Billerica, Mass., USA) and 3,3,5,5-tetramethylbenzidine (TMB) Pierce HRP substrate (Thermo Scientific, Rockford, Ill., USA). The absorbance is recorded at 450 nm using a PerkinElmer Envision plate reader. The absorbance values are normalized to the maximal response of control cells treated with human insulin (100 nM, for the hIR-A and hIR-B assays) or 10 nM IGF-1 (for the hIGF-1R assay). The data are analyzed using a 4-parameter (curve maximum, curve minimum, EC50, Hill slope) logistic (sigmoidal) nonlinear regression routine (XLFit version 4.0: Activity Base, IDBS). Functional potency is reported as the concentration eliciting a half-maximal response (EC50), with values shown as the geometric mean± the standard error of the mean (SEM), with the number of replicate determinations indicated by "n".

Compound 330 is an agonist for hIR-A and hIR-B and is selective for insulin receptors compared to hIGF-1R (Table 2).

TABLE 2

Human Insulin Receptor (hIR-A and hIR-B) and Human Insulin-like Growth Factor-1 Receptor (hIGF-1R) Phosphorylation in 293 Cells

| Sample | Receptor Phosphorylation EC50, nM (SEM, n) | | |
|---|---|---|---|
| | hIR-A | hIR-B | hIGF-1R |
| Compound 330 | 39.2 (5.8, n = 12) | 34.8 (4.9, n = 13) | 4270 (611, n = 3) |
| Human insulin | 2.65 (0.31, n = 12) | 2.28 (0.28, n = 13) | 254 (29, n = 6) |
| IGF-1 | 91.5 (12.1, n = 11) | 253 (36, n = 4) | 2.15 (0.22, n = 6) |

Evaluation of In Vivo Potency in a Rat Model of Type 1 Diabetes

The effects of Compound 330 are investigated in a streptozotocin (STZ)-treated rat diabetes model. Male Sprague-Dawley rats, 400-425 gram body weight, are obtained from Harlan Labs, Indianapolis, Ind. After acclimation for approximately one week, the rats are anesthetized with isoflurane and given a single injection of streptozotocin (Zanosar®, item #89256, Teva Parenteral Medicines, 40 mg/kg IV). The rats are used in studies three days after injection of the streptozotocin; only animals with non-fasted blood glucose between 400-550 mg/dl are used in these studies.

Rats are distributed into groups to provide comparable variance in blood glucose and body weight; rats are randomized using Block Randomized Allocation Tool. Blood glucose is measured using Accucheck Aviva glucometer (Roche). STZ-treated rats are given a single subcutaneous (SC) injection of Compound 330 or vehicle, Sterile Normal Saline (0.9% w/v sodium chloride solution). Blood samples for glucose measurements are collected by tail bleed. The animals have free access to food and water throughout the experiment. Plasma samples from these studies are sent for analysis of compound levels.

Blood glucose levels for Compound 330 are measured at three dosage levels, 30, 100, 300 nmol/kg in (STZ)-treated rats. Blood glucose is measured 0, 0.5, 1, 2, 4, 6, 8, 10, 12, 24, 36, 48, 72, and 96 hours after injection. Data shown are mean± (standard error mean) SEM (n=5). Statistical analysis was performed using JMP software, and treatment groups are compared to a vehicle control group (*P<0.05).

Compound 330 shows glucose lowering over the control group of up to 76% with a 100 nmol/kg dose at 8 hours and up to 89% with a 300 nmol/kg dose at 24 hours (Table 3).

TABLE 3

Blood Glucose Levels over Time after Administration of Compound 330 (mg/dL)

| Time (hours) | Compound 330 100 nmol/kg (SEM) | Compound 330 300 nmol/kg (SEM) | Vehicle (SEM) |
|---|---|---|---|
| 0 | 484 (28) | 532 (13) | 552 (6) |
| 0.5 | 471 (52) | 539 (18) | 541 (7) |
| 1 | 470 (50) | 519 (8) | 550 (14) |
| 2 | 373 (55) | 423 (30) | 498 (12) |
| 4 | 301 (53) | 139 (24) | 512 (30) |
| 6 | 196 (46) | 111 (41) | 456 (13) |
| 8 | 111 (17) | 90 (15) | 466 (23) |
| 10 | 136 (18) | 119 (12) | 488 (31) |
| 12 | 280 (61) | 141 (25) | 567 (20) |
| 24 | 156 (48) | 59 (6) | 528 (8) |
| 36 | 386 (76) | 98 (7) | 590 (10) |
| 48 | 330 (66) | 121 (26) | 572 (13) |
| 72 | 409 (58) | 451 (22) | 553 (13) |
| 96 | 480 (51) | 503 (9) | 562 (10) |

Sequences

Polypeptide Sequence (SEQ ID NO: 1)
GIVEQCCTSICSLYQLENYCGSGPAGGTSESATPESGPGSEPATSGSETP
GTSESATPESGPGSEPATSGSETPGTSESATPESGPGTSTEPSEGSAPGS
PAGSPTSTEEGTSESATPESGPGSEPATSGSETPGTSESATPESGPGSPA
GSPTSTEEGSPAGSPTSTEEGTSTEPSEGSAPGTSESATPESGPGTSESA
TPESGPGTSESATPESGPGSEPATSGSETPGSEPATSGSETPGSPAGSPT
STEEGTSTEPSEGSAPGTSTEPSEGSAPGSEPATSGSETPGTSESATPES
GPGTSTEPSEGSAPG Polypeptide Sequence (SEQ ID NO: 2)
FVNQHLCGSHLVEALYLVCGERGFFYTKPT Polypeptide Sequence (SEQ ID NO: 3)
MKKNIAFLLASMFVFSIATNAYAGSPGTSTEPSEGSAPGTSESATPESGP
GTSESATPESGPGGAPGSGSGSGGSGGIEGRFVNQHLCGSHLVEALYLVC
GERGFFYTKPTRGGGGRGIVEQCCTSICSLYQLENYCGSGPAGGTSESAT
PESGPGSEPATSGSETPGTSESATPESGPGSEPATSGSETPGTSESATPE
SGPGTSTEPSEGSAPGSPAGSPTSTEEGTSESATPESGPGSEPATSGSET
PGTSESATPESGPGSPAGSPTSTEEGSPAGSPTSTEEGTSTEPSEGSAPG
TSESATPESGPGTSESATPESGPGTSESATPESGPGSEPATSGSETPGSE
PATSGSETPGSPAGSPTSTEEGTSTEPSEGSAPGTSTEPSEGSAPGSEPA
TSGSETPGTSESATPESGPGTSTEPSEGSAPG

We claim:

1. A compound comprising an A chain and a B chain, wherein the amino acid sequence of the A chain is SEQ ID NO: 1 and the amino acid sequence of the B chain is SEQ ID NO: 2, and wherein the A and B chains contain a disulfide bond between the cysteine at position 7 of the A chain and the cysteine at position 7 of the B chain, a disulfide bond between the cysteine at position 20 of the A chain and the cysteine at position 19 of the B chain, and a disulfide bond between the cysteine at position 6 of the A chain and the cysteine at position 11 of the A chain.

2. A pharmaceutical composition comprising the compound of claim 1 and one or more pharmaceutically acceptable excipients.

3. A method of treating diabetes in a patient comprising administering to a patient in need thereof an effective amount of the compound of claim 1.

4. A method of treating diabetes in a patient comprising administering to a patient in need thereof an effective amount of the composition of claim 2.

5. A method of treating hyperglycemia in a patient comprising administering to a patient in need thereof an effective amount of the compound of claim 1.

6. A method of treating hyperglycemia in a patient comprising administering to a patient in need thereof an effective amount of the composition of claim 2.

* * * * *